United States Patent [19]
Foglietti

[11] Patent Number: 5,116,370
[45] Date of Patent: May 26, 1992

[54] BREAST PROSTHESIS WITH FEMALE AND MALE ADAPTER SNAPS

[76] Inventor: Mark A. Foglietti, 32640 N. Burr Oak Dr., Solon, Ohio 44139

[21] Appl. No.: 673,361

[22] Filed: Mar. 22, 1991

[51] Int. Cl.$^5$ .................................................. A61F 2/12
[52] U.S. Cl. ......................................................... 623/8
[58] Field of Search ........................................ 623/7, 8

[56] References Cited

U.S. PATENT DOCUMENTS

| | | | |
|---|---|---|---|
| 3,366,975 | 2/1968 | Pangman | 623/8 |
| 4,426,742 | 1/1984 | Prahl | 623/8 |
| 4,433,440 | 2/1984 | Cohen | 623/8 |
| 4,531,244 | 7/1985 | Hamas | 623/8 |
| 4,605,412 | 8/1986 | LaForest et al. | 623/8 |
| 4,950,292 | 8/1990 | Audretsch | 623/8 |
| 4,984,585 | 1/1991 | Austad | 623/8 |

FOREIGN PATENT DOCUMENTS

0054197 6/1982 Fed. Rep. of Germany .......... 623/8

*Primary Examiner*—Randall L. Green
*Assistant Examiner*—G. Gualtieri
*Attorney, Agent, or Firm*—Longacre & White

[57] ABSTRACT

An improved breast prosthesis with female and male connector elements for insertion under the subcutaneous tissue or in a retromuscular pocket, the prosthesis being comprised of a textured or smooth outer shell a minimal projection female connector element attached as a integral part of the anterior surface of the outer shell of the breast prosthesis, and a minimal projection male connector element attached as an integral part of the posterior surface of the outer shell of the breast prosthesis, wherein the connector elements are either bonded or molded into the outer shell as an integral part of the outer shell.

12 Claims, 1 Drawing Sheet

BREAST PROSTHESIS WITH FEMALE AND MALE ADAPTER SNAPS

BACKGROUND OF THE INVENTION

1. Field of the Invention

This invention is for an improved breast prosthesis which allows for the stacking of smaller sized implants upon large sized implants without fear of slippage and subsequent cosmetic deformity.

2. Description of the Prior Art

Breast reconstruction after mastectomy and for augmentation mammoplasty utilizing silicone gel breast implants is a well recognized surgical procedure. The art has evolved over the years with advances in both silicone and materials technology and in the improvement of the outer shell of the silicone gel breast prosthesis.

In relatively recent years, the polyurethane outer shell silicone gel prosthesis has been invented. The greater coefficient of friction of the polyurethane outer shell has allowed surgeons to stack the implants one on top of another in a surgically developed chest pocket. This has allowed surgeons to stack a smaller implant on top of a larger sized implant, thus giving the augmented or reconstructed breast not only greater volume but also a greater dimensional projection and the proper conical appearance of an anatomically correct breast.

Regrettably, this effect is difficult to achieve with the standard silicone outer shell silicone gel breast prosthesis, with either a textured or smooth shell, since these prostheses maintain a lower coefficient of friction when in contact with one another. Consequently, this can result in the prostheses slipping from their stacked position, resulting in a significant cosmetic deformity as well as frictional stress to the two opposing silicone surfaces.

SUMMARY OF THE INVENTION

The present invention, to be used in augmentation mammoplasty and reconstructive breast surgery, is for an improved surgical breast prosthesis which can be stacked one on top of another, without the prostheses slipping from their stacked position causing cosmetic deformity.

In particular, this invention relates to an improved breast prosthesis outer shell, which is comprised of connector elements which enable positive attachment of one prosthetic member to another. The embodiment herein described and considered preferred embodies a minimal projection female connector element attached as a part of the anterior surface of the outer shell of the breast prosthesis and a minimal projection male connector element attached as a part of the posterior surface of the outer shell. The breast prosthesis is inserted either under the subcutaneous tissue or in a retromuscular pocket of the patient. In general, both the prosthesis and the connector elements are to be made out of silicone. However, other breast prostheses to which this invention may be applied include a saline filled silicone breast prosthesis, a double lumen silicone-saline breast prosthesis, a bio-oncotic gel breast prosthesis, and any other breast implants which may or could be stacked. The connector elements can be either a snap lock or a twist lock and can be either bonded to the outer shell of the prosthesis or molded into the outer shell as an integral part of the shell. The female and male connector elements should be round in shape.

It is important that the female snap site have a minimal projection from the implant, and be located on the anterior surface of the implant, so as to prevent any conceivable visible or palpable anterior breast flap deformity on the patient's chest. The male snap can also be round with a minimal projection, but with enough of a projection to maintain a locked position when snap locked or twist locked into the female recipient snap. The male connector means' positioning at the center of the posterior surface of the outer shell of the prosthesis prevents any noticeable deformity on the patient's anterior chest.

While all breast prosthesis should have an anterior female connector element and posterior male connector element, it is also feasible to have some breast prostheses that uses the lock connector elements with only a posterior male connector element to be used as the last or top prosthesis in the stack.

In the operating room during the breast reconstruction or augmentation procedure, the smaller volume implants of the present invention will be united by snapping them onto larger volume implants and thus achieving greater overall projection and volume which can not be achieved by the use of a single large volume implant alone.

Previously, the low coefficient of friction maintained by the silicone outer shell silicone gel prosthesis, as compared to the polyurethane outer shell prosthesis, has prohibited stacking of this type of breast prosthesis. This connector invention herein using a snap or twist lock connector element concept will allow a surgeon to stack any silicone gel breast prosthesis that utilizes a similar connector concept. With the prosthesis in the locked position, the prosthesis will not slide off from one another, will not reverse positions in the soft tissue pocket, and will not distort when compression of the operated breast occurs.

The number and size of the implants to be used is determined by the surgeon at the time of surgery to fit the needs of the individual patient.

DETAILED DESCRIPTION OF THE PREFERRED EMBODIMENTS

Figure 1:
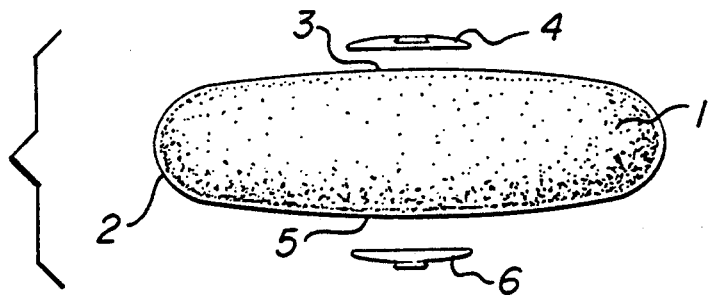
FIG. 1 is an exploded side view of the present invention.
Figure 2:
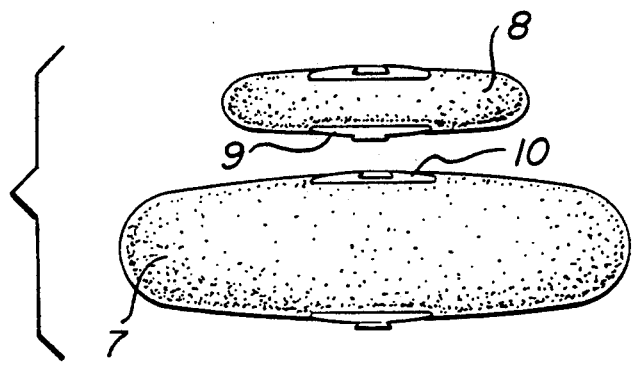
FIG. 2 is a side view of a smaller volume prosthesis prior to being stacked on top of a larger volume prosthesis of the present invention.

The present invention as illustrated in FIG. 1 shows the silicone gel breast prosthesis 1 with an outer shell 2. On the anterior side 3 of the breast prosthesis 1 is a round female silicone snap 4. On the posterior side 5 of the silicone gel breast prosthesis 1 is a round male silicone snap 6. These snaps 4 and 6 may be either bonded to the outer shell of the breast prosthesis or, in a preferred embodiment, may be molded into the outer shell as an integral part of the shell. It is also preferable that the snaps be round and made out of silicone, to lessen the chances of immunogenic reaction.

When implanting the prostheses under the subcutaneous tissue or in a retromuscular pocket of the patient, a larger volume silicone based gel prosthesis 7 is fitted inside the patient. It is then determined, by measurements and fittings, how large and how many silicone gel prostheses will be utilized. Outside of the body of the patient, a lesser volume silicone gel breast prosthesis 8 is positioned above the larger volume breast prosthesis 7.

Figure 3:
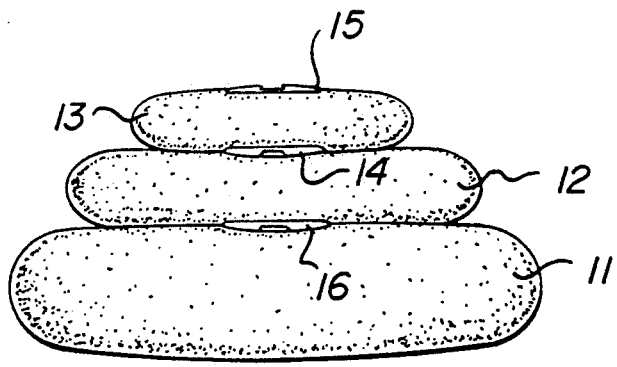
FIG. 3 is a side view of the prostheses of the present invention stacked together.
Figure 4:
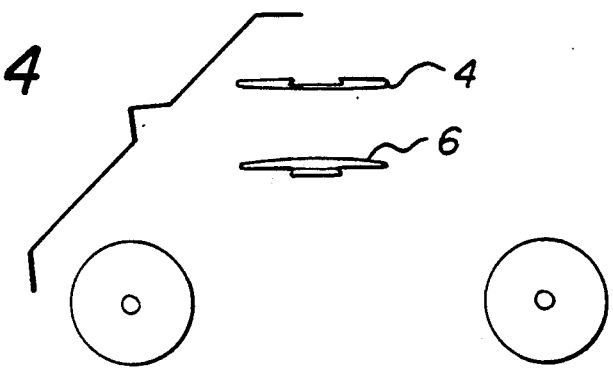
FIG. 4 is a side view of the anterior female snap and the posterior male snap, and an anterior and posterior view of the invention.

The number of silicone gel based prostheses which may be stacked is limited only by the size of the patient and the desired cosmetic effect. FIG. 3 shows three silicone gel breast prostheses stacked and locked together. The largest volume silicone gel breast prosthesis 11 resides at the bottom of the stack, with the next larger or middle sized silicone gel breast prosthesis 12 stacked and locked on top of the largest silicone gel breast prosthesis 11, and the smallest gel breast prosthesis 13 stacked and locked on top of the next larger or middle sized silicone gel breast prosthesis 12. These breast prostheses are stacked and locked together on one another outside of the patient's body two at a time, by applying pressure against each prosthesis. Prostheses 11 and 12 are locked together first by aligning the female snap on the anterior side of prosthesis 11 with the male snap on the posterior side of prosthesis 12 and pushing the two prostheses together until they snap together. Prosthesis 15 is then attached to prosthesis 12 in the same manner. Thus, prostheses 12 and 13 are joined together by a locked interface 14, and prosthesis 11 and 12 are joined together by a locked interface 16.

While the preferred embodiment for this invention is that the female and male snaps be round and made out of silicone, the snaps may be made out of any substance that will not cause an immunogenic response, nor do they have to be round. The connector elements do not have to be snaps but may be any sort of locking mechanism, including a turn or twist locking mechanism.

The outer shell of the may have an additional coating, such as a polyurethane coating, and it may be smooth or textured.

While this device is directed to a silicone gel based breast prosthesis, it can be used in any breast prosthesis where stacking is required. Other breast prostheses which may be used include a saline filled silicone breast prosthesis, double lumen silicone-saline breast prosthesis, and a bio-oncotic gel breast prosthesis.

Although particular embodiments of the present invention have been described and illustrated herein, it should be recognized that modifications and variations may readily occur to those skilled in the art and that such modifications and variations may be made without departing from the spirit and scope of the invention. Consequently, the invention as claimed below may be practiced otherwise than as specifically described above.

What is claimed is:

1. A breast prosthesis for surgical insertion comprising:
    a first implant element having a first outer shell enveloping a fluid filler;
    a second implant element having a second outer shell also enveloping a fluid filler;
    a first connector means attached to said first outer shell of said first implant element for connecting and attaching to a second connector means attached to said second outer shell of said second implant element;
    said first and second connector means configured for releasable interconnection one to the other.

2. A breast prosthesis according to claim 1, wherein said first and second connector means are bonded to said first and second outer shells, respectively.

3. A breast prosthesis according to claim 1, wherein said first and second connector means are molded into said first and second outer shells, respectively, as an integral part of said outer shells.

4. A breast prosthesis according to claim 1, wherein said connector means are round.

5. A breast prosthesis according to claim 1, wherein said connector means are snap locks.

6. A breast prosthesis according to claim 1, wherein said connector means comprise cooperatively engagable members adapted to be relatively twisted for engagement and disengagement.

7. A breast prosthesis according to claim 1, wherein said first connector means comprises at least one female snap element on an anterior surface of said first outer shell and said second connector means comprises at least one male snap element on a posterior surface of said second outer shell, said at least one female snap element and said at least one male snap element adapted for connecting one to the other.

8. A breast prosthesis according to claim 1, said outer shells of said first and second implant elements are silicone and said fluid filler is selected from the group consisting of silicone gel, saline, and bio-oncotic gel.

9. A breast prosthesis according to claim 1, wherein at least one of said first and second outer shells is textured.

10. A breast prosthesis according to claim 1, wherein at least one of said first and second outer shells is smooth.

11. A breast prosthesis according to claim 1, at least one of said first and second outer shells further comprises an additional coating.

12. A breast prosthesis according to claim 11, wherein said additional coating is polyurethane.

* * * * *